US006221837B1

United States Patent
Ertl et al.

(10) Patent No.: US 6,221,837 B1
(45) Date of Patent: *Apr. 24, 2001

(54) INSULIN DERIVATIVES WITH INCREASED ZINC BINDING

(75) Inventors: Johann Ertl, Bremthal; Paul Habermann, Eppstein; Karl Geisen, Frankfurt; Gerhard Seipke, Hofheim, all of (DE)

(73) Assignee: Aventis Pharma Deutschland GmbH, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/900,574

(22) Filed: Jul. 25, 1997

(30) Foreign Application Priority Data

Jul. 26, 1996 (DE) ................................ 196 30 242

(51) Int. Cl.[7] ........................... C07K 14/62; A61K 33/30; A61K 38/28

(52) U.S. Cl. ................................ 514/3; 514/4; 514/866; 530/303; 530/304

(58) Field of Search ...................... 514/3, 4, 866; 530/303, 304

(56) References Cited

U.S. PATENT DOCUMENTS

| | | |
|---|---|---|
| 4,476,118 * | 10/1984 | Brange et al. ............... 424/178 |
| 4,569,794 | 2/1986 | Smith et al. . |
| 4,701,440 | 10/1987 | Grau . |
| 5,008,241 * | 4/1991 | Markussen et al. .............. 514/3 |
| 5,177,058 | 1/1993 | Dörschug . |
| 5,227,293 | 7/1993 | Stengelin et al. . |
| 5,284,933 | 2/1994 | Döbeli et al. . |
| 5,310,663 | 5/1994 | Döbeli et al. . |
| 5,358,857 | 10/1994 | Stengelin et al. . |
| 5,656,722 | 8/1997 | Dörschug . |

FOREIGN PATENT DOCUMENTS

| | | |
|---|---|---|
| 37 39 347 A1 | 6/1989 | (DE) . |
| 0 180 920 A2 | 5/1986 | (EP) . |
| 0 211 299 A2 | 2/1987 | (EP) . |
| 0 227 938 A2 | 7/1987 | (EP) . |
| 0 229 998 A2 | 7/1987 | (EP) . |
| 0 286 956 A2 | 10/1988 | (EP) . |
| 0 305 760 A2 | 3/1989 | (EP) . |
| 0 347 781 A2 | 12/1989 | (EP) . |
| 0 368 187 A2 | 5/1990 | (EP) . |
| 0 453 969 A1 | 10/1991 | (EP) . |
| 0 184 355 B1 | 1/1992 | (EP) . |
| 0 600 372 A1 | 6/1994 | (EP) . |
| 0 668 292 A2 | 8/1995 | (EP) . |
| WO 91/03550 | 3/1991 | (WO) . |

OTHER PUBLICATIONS

Manallack et al. J. Med. Chem. 28:1522–1526, 1985.*
Ljungquist et al. Eur. J. Biochem. 186:563–569, 1989.*
Katzung, B.G. Basic & Clinical Pharmacology, 5th ed. Appleton & Lange, Norwalk CT, 1992.*
Brang et al., "Monomeric insulins and Their Experimental and Clinical Implications," *Diabetes Care*, vol. 13, No. 9, pp. 923–954, 1990.
Kang et al., "Subcutaneous Insulin Absorption Explained by Insulin's Physicochemical Properties—Evidence From Absorption Studies of Soluble Human Insulin and Insulin Analogues In Humans," *Diabetes Care*, vol. 14, pp. 942–948, 1991.
Smith et al., "Structural stability in the 4–zinc human insulin hexamer," *Proc. Nat'l. Acad. Sci. USA*, vol. 81, pp. 7093–7097, 1984.
Marshall et al., "Protein Oligomer Composition, Preparation of Monomers and Constituent Chains", *Practical Protein Chemistry–A Handbook*, A. Darbre, Ed., pp. 49–53, 1986.
Dixon et al., "Regeneration of Insulin Activity From the Separated and Inactive A and B Chains," *Nature*, No. 4752, pp. 721–724, Nov. 26, 1960.
Kemmler et al., "Studies on the Conversion of Proinsulin to Insulin I. Conversion In Vitro with Trypsin and Carboxypeptidase B," *The Journal of Biological Chemistry*, vol. 246, No. 22, pp. 6786–6791, 1971.
Michele C. Smith et al., "Chelating Peptide–immobilized Metal Ion Affinity Chromatography", The Journal of Biological Chemistry, vol. 263, No. 15, May 25, 1988, p. 7211–7215.

* cited by examiner

Primary Examiner—Christine J. Saoud
(74) Attorney, Agent, or Firm—Finnegan, Henderson, Farabow, Garrett and Dunner, L.L.P.

(57) ABSTRACT

Insulin derivatives with increased zinc binding $$
\begin{array}{c}
\text{Gly}\text{—}\overset{(A\,6)}{\underset{(A\,1)}{\text{Cys}}}\overset{\phantom{(}S\text{—}S\phantom{)}}{\text{—}}\text{Cys}\text{—}\overset{(A\,20)}{\underset{(A\,11)}{\text{Cys}}}\text{—}\text{Cys}\text{—}R^3\text{—}\text{OH} \\
\phantom{Gly—}\big|\phantom{\text{Cys}}S\phantom{\text{Cys}}\phantom{\text{Cys}}\big|\phantom{\text{Cys}}S \\
\phantom{Gly—}\big|\phantom{\text{Cys}}S\phantom{\text{Cys}}\phantom{\text{Cys}}\big|\phantom{\text{Cys}}S \\
R^1\text{—}\underset{(B\,1)}{\text{Cys}}\text{—}\underset{(B\,7)}{\phantom{\text{Cys}}}\phantom{\text{—}}\text{Cys}\text{—}\underset{(B\,19)}{\phantom{\text{Cys}}}\text{—}Y\text{—}\underset{(B\,30)}{Z}
\end{array}
$$ (I)

where Z is a histidine residue or a peptide having 2 to 35 genetically encodable amino acid residues, having 1 to 5 histidine residues, are suitable for the production of pharmaceutical preparations for the treatment of diabetes. Insulins of the formula I form complexes with zinc$^{++}$, comprising an insulin hexamer and approximately 5 to 9 mol of zinc$^{++}$ per hexamer.

22 Claims, No Drawings

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 21 amino acids
      (B) TYPE: Amino acid
      (C) STRANDEDNESS: Single
      (D) TOPOLOGY: linear

```
        (ii) MOLECULE TYPE: Protein (vi) ORIGINAL SOURCE:
             (A) ORGANISM: Escherichia coli (ix) FEATURE:
             (A) NAME/KEY: Protein
             (B) LOCATION: 1..21

(xi) SEQUENCE DESCRIPTION: SEQ ID NO: 1:

Gly Ile Val Glu Gln Cys Cys Thr Ser Ile Cys Ser Leu Tyr Gln
1               5                   10                  15

Leu Glu Asn Tyr Cys Asn
                20

(2) INFORMATION FOR SEQ ID NO: 2:

(i) SEQUENCE CHARACTERISTICS:
            (A) LENGTH: 30 amino acids
            (B) TYPE: Amino acid
            (C) STRANDEDNESS: Single
            (D) TOPOLOGY: linear (ii) MOLECULE TYPE: Protein (vi) ORIGINAL SOURCE:
             (A) ORGANISM: Escherichia coli (ix) FEATURE:
             (A) NAME/KEY: Protein
             (B) LOCATION: 1..30

(xi) SEQUENCE DESCRIPTION: SEQ ID NO: 2:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
                20                  25                  30

(2) INFORMATION FOR SEQ ID NO: 3:

(i) SEQUENCE CHARACTERISTICS:
            (A) LENGTH: 65 amino acids
            (B) TYPE: Amino acid
            (C) STRANDEDNESS: Single
            (D) TOPOLOGY: linear (ii) MOLECULE TYPE: Protein (vi) ORIGINAL SOURCE:
             (A) ORGANISM: Escherichia coli (ix) FEATURE:
             (A) NAME/KEY: Protein
             (B) LOCATION: 1..65

(xi) SEQUENCE DESCRIPTION: SEQ ID NO: 3:

Met Ala Thr Thr Ser Thr Gly Asn Ser Ala Arg Phe Val Asn Gln His
1               5                   10                  15

Leu Cys Gly Ser His Leu Val Glu Ala Leu Tyr Leu Val Cys Gly Glu
                20                  25                  30

Arg Gly Phe Phe Tyr Thr Pro Lys Thr His His Arg Gly Ile Val Glu
                35                  40                  45

Gln Cys Cys Thr Ser Ile Cys Ser Leu Tyr Gln Leu Glu Asn Tyr Cys
    50                  55                  60

Gly
65
```

(2) INFORMATION FOR SEQ ID NO: 4:

(i) SEQUENCE CHARACTERISTICS:
        (A) LENGTH: 53 amino acids
        (B) TYPE: Amino acid
        (C) STRANDEDNESS: Single
        (D) TOPOLOGY: linear (ii) MOLECULE TYPE: Protein (vi) ORIGINAL SOURCE:
        (A) ORGANISM: Escherichia coli (ix) FEATURE:
        (A) NAME/KEY: Protein
        (B) LOCATION: 1..53

(xi) SEQUENCE DESCRIPTION: SEQ ID NO: 4:

```
Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr His His
            20                  25                  30

Gly Ile Val Glu Gln Cys Cys Thr Ser Ile Cys Ser Leu Tyr Gln Leu
        35                  40                  45

Glu Asn Tyr Cys Gly
    50
```

(2) INFORMATION FOR SEQ ID NO: 5:

(i) SEQUENCE CHARACTERISTICS:
        (A) LENGTH: 66 amino acids
        (B) TYPE: Amino acid
        (C) STRANDEDNESS: Single
        (D) TOPOLOGY: linear (ii) MOLECULE TYPE: Protein (vi) ORIGINAL SOURCE:
        (A) ORGANISM: Escherichia coli (ix) FEATURE:
        (A) NAME/KEY: Protein
        (B) LOCATION: 1..66

(xi) SEQUENCE DESCRIPTION: SEQ ID NO: 5:

```
Met Ala Thr Thr Ser Thr Gly Asn Ser Ala Arg Phe Val Asn Gln His
 1               5                  10                  15

Leu Cys Gly Ser His Leu Val Glu Ala Leu Tyr Leu Val Cys Gly Glu
            20                  25                  30

Arg Gly Phe Phe Tyr Thr Pro Lys Thr Ala His His Arg Gly Ile Val
            35                  40                  45

Glu Gln Cys Cys Thr Ser Ile Cys Ser Leu Tyr Gln Leu Glu Asn Tyr
    50                  55                  60

Cys Gly
65
```

(2) INFORMATION FOR SEQ ID NO: 6:

(i) SEQUENCE CHARACTERISTICS:
        (A) LENGTH: 55 amino acids
        (B) TYPE: Amino acid
        (C) STRANDEDNESS: Single
        (D) TOPOLOGY: linear (ii) MOLECULE TYPE: Protein (vi) ORIGINAL SOURCE:
        (A) ORGANISM: Escherichia coli (ix) FEATURE:
              (A) NAME/KEY: Protein
              (B) LOCATION: 1..55

(xi) SEQUENCE DESCRIPTION: SEQ ID NO: 6:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Ala His
                20                  25                  30

His Arg Gly Ile Val Glu Gln Cys Cys Thr Ser Ile Cys Ser Leu Tyr
            35                  40                  45

Gln Leu Glu Asn Tyr Cys Gly
    50                  55

(2) INFORMATION FOR SEQ ID NO: 7:

(i) SEQUENCE CHARACTERISTICS:
              (A) LENGTH: 67 amino acids
              (B) TYPE: Amino acid
              (C) STRANDEDNESS: Single
              (D) TOPOLOGY: linear (ii) MOLECULE TYPE: Protein (vi) ORIGINAL SOURCE:
              (A) ORGANISM: Escherichia coli (ix) FEATURE:
              (A) NAME/KEY: Protein
              (B) LOCATION: 1..67

(xi) SEQUENCE DESCRIPTION: SEQ ID NO: 7:

Met Ala Thr Thr Ser Thr Gly Asn Ser Ala Arg Phe Val Asn Gln His
1               5                   10                  15

Leu Cys Gly Ser His Leu Val Glu Ala Leu Tyr Leu Val Cys Gly Glu
                20                  25                  30

Arg Gly Phe Phe Tyr Thr Pro Lys Thr Ala Ala His His Arg Gly Ile
            35                  40                  45

Val Glu Gln Cys Cys Thr Ser Ile Cys Ser Leu Tyr Gln Leu Glu Asn
    50                  55                  60

Tyr Cys Gly
65

(2) INFORMATION FOR SEQ ID NO: 8:

(i) SEQUENCE CHARACTERISTICS:
              (A) LENGTH: 55 amino acids
              (B) TYPE: Amino acid
              (C) STRANDEDNESS: Single
              (D) TOPOLOGY: linear (ii) MOLECULE TYPE: Protein (vi) ORIGINAL SOURCE:
              (A) ORGANISM: Escherichia coli (ix) FEATURE:
              (A) NAME/KEY: Protein
              (B) LOCATION: 1..55

(xi) SEQUENCE DESCRIPTION: SEQ ID NO: 8:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Ala Ala
                20                  25                  30

```
His His Gly Ile Val Glu Gln Cys Cys Thr Ser Ile Cys Ser Leu Tyr
        35                  40                  45

Gln Leu Glu Asn Tyr Cys Gly
    50                  55
```

(2) INFORMATION FOR SEQ ID NO: 9:

(i) SEQUENCE CHARACTERISTICS:
        (A) LENGTH: 54 amino acids
        (B) TYPE: Amino acid
        (C) STRANDEDNESS: Single
        (D) TOPOLOGY: linear (ii) MOLECULE TYPE: Protein (vi) ORIGINAL SOURCE:
        (A) ORGANISM: Escherichia coli (ix) FEATURE:
        (A) NAME/KEY: Protein
        (B) LOCATION: 1..54

(xi) SEQUENCE DESCRIPTION: SEQ ID NO: 9:

```
Phe Val Asn Gln His Leu Cys Gly Ser His Leu Val Glu Ala Leu Tyr
1                   5                  10                  15

Leu Val Cys Gly Glu Arg Gly Phe Phe Tyr Thr Pro Lys Thr Ala His
            20                  25                  30

His Gly Ile Val Glu Gln Cys Cys Thr Ser Ile Cys Ser Leu Tyr Gln
        35                  40                  45

Leu Glu Asn Tyr Cys Gly
    50
```

(2) INFORMATION FOR SEQ ID NO: 10:

(i) SEQUENCE CHARACTERISTICS:
        (A) LENGTH: 39 base pairs
        (B) TYPE: Nucleic acid
        (C) STRANDEDNESS: Single
        (D) TOPOLOGY: linear (ii) MOLECULE TYPE: DNA (genomic)

(ix) FEATURE:
        (A) NAME/KEY: exon
        (B) LOCATION: 1..39

(xi) SEQUENCE DESCRIPTION: SEQ ID NO: 10:

TTTTTTGTCG ACCTATTAGC CGCAGTAGTT CTCCAGCTG                    39

(2) INFORMATION FOR SEQ ID NO: 11:

(i) SEQUENCE CHARACTERISTICS:
        (A) LENGTH: 31 base pairs
        (B) TYPE: Nucleic acid
        (C) STRANDEDNESS: Single
        (D) TOPOLOGY: linear (ii) MOLECULE TYPE: DNA (genomic)

(ix) FEATURE:
        (A) NAME/KEY: exon
        (B) LOCATION: 1..31

(xi) SEQUENCE DESCRIPTION: SEQ ID NO: 11:

GATGCCGCGG TGGTGGGTCT TGGGTGTGTA G                           31

(2) INFORMATION FOR SEQ ID NO: 12:

(i) SEQUENCE CHARACTERISTICS:
        (A) LENGTH: 31 base pairs
        (B) TYPE: Nucleic acid
        (C) STRANDEDNESS: Single
        (D) TOPOLOGY: linear (ii) MOLECULE TYPE: DNA (genomic)

(ix) FEATURE:
        (A) NAME/KEY: exon
        (B) LOCATION: 1..31

(xi) SEQUENCE DESCRIPTION: SEQ ID NO: 12:

ACCCAAGACC CACCACCGCG GCATCGTGGA G                                      31

(2) INFORMATION FOR SEQ ID NO: 13:

(i) SEQUENCE CHARACTERISTICS:
        (A) LENGTH: 34 base pairs
        (B) TYPE: Nucleic acid
        (C) STRANDEDNESS: Single
        (D) TOPOLOGY: linear (ii) MOLECULE TYPE: DNA (genomic)

(ix) FEATURE:
        (A) NAME/KEY: exon
        (B) LOCATION: 1..34

(xi) SEQUENCE DESCRIPTION: SEQ ID NO: 13:

GATGCCGCGG TGGTGCGCGG TCTTGGGTGT GTAG                                   34

(2) INFORMATION FOR SEQ ID NO: 14:

(i) SEQUENCE CHARACTERISTICS:
        (A) LENGTH: 34 base pairs
        (B) TYPE: Nucleic acid
        (C) STRANDEDNESS: Single
        (D) TOPOLOGY: linear (ii) MOLECULE TYPE: DNA (genomic)

(ix) FEATURE:
        (A) NAME/KEY: exon
        (B) LOCATION: 1..34

(xi) SEQUENCE DESCRIPTION: SEQ ID NO: 14:

ACCCAAGACC GCGCACCACC GCGGCATCGT GGAG                                   34

(2) INFORMATION FOR SEQ ID NO: 15:

(i) SEQUENCE CHARACTERISTICS:
        (A) LENGTH: 37 base pairs
        (B) TYPE: Nucleic acid
        (C) STRANDEDNESS: Single
        (D) TOPOLOGY: linear (ii) MOLECULE TYPE: DNA (genomic)

(ix) FEATURE:
        (A) NAME/KEY: exon
        (B) LOCATION: 1..37

(xi) SEQUENCE DESCRIPTION: SEQ ID NO: 15:

GATGCCGCGA TGATGCGCCG CGGTCTTGGG TGTGTAG                                37

(2) INFORMATION FOR SEQ ID NO: 16:

(i) SEQUENCE CHARACTERISTICS:
        (A) LENGTH: 37 base pairs

```
        (B) TYPE: Nucleic acid
        (C) STRANDEDNESS: Single
        (D) TOPOLOGY: linear (ii) MOLECULE TYPE: DNA (genomic)

(ix) FEATURE:
        (A) NAME/KEY: exon
        (B) LOCATION: 1..37

(xi) SEQUENCE DESCRIPTION: SEQ ID NO: 16:

ACCCAAGACC GCGGCGCATC ATCGCGGCAT CGTGGAG                                    37

(2) INFORMATION FOR SEQ ID NO:17:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

His His His His Arg Ala His His Ala His His Arg Ala Ala His His
1               5                   10                  15

Arg (2) INFORMATION FOR SEQ ID NO:18:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Ala Ala His His
```

INSULIN DERIVATIVES WITH INCREASED ZINC BINDING

BACKGROUND OF THE INVENTION

The pharmacokinetics of subcutaneously administered insulin is dependent on its association behavior. Insulin forms hexamers in neutral aqueous solution. To get from the tissue into the blood stream and to the site of action, insulin must first pass through the walls of the capillaries. It is assumed that this is only possible for monomeric and for dimeric insulin—but not possible or only slightly possible for hexameric insulins or relatively high molecular weight associates (Brange et al., Diabetes Care: 13 (1990), pages 923–954; Kang et al., Diabetes Care: 14 (1991), pages 942–948). The dissociation of the hexamer is therefore a prerequisite for rapid passage from the subcutaneous tissue into the blood stream.

The association and aggregation behavior of insulin is affected by zinc$^{++}$, which leads to a stabilization of the hexamer and at pHs around the neutral point to the formation of relatively high molecular weight aggregates until precipitation occurs. Zinc$^{++}$ as an additive to an unbuffered human insulin solution (pH 4), however, only slightly affects the profile of action. Although such solution is rapidly neutralized in the subcutaneous tissue on injection and insulin-zinc complexes are formed, the natural zinc binding of human insulin is insufficient to stabilize hexamers and higher aggregates. Therefore, by addition of zinc$^{++}$, the release of human insulin is not markedly delayed and a strong depot effect is not achieved. Known insulin hexamers have a content of approximately 2 mol of zinc per mole of insulin hexamer (Blundell et al., Adv. Protein Chem.: 26 (1972), pages 323–328). Two zinc molecules per insulin hexamer are firmly bound to the insulin hexamer and cannot be removed by normal dialysis. So-called 4-zinc insulin crystals have been described, but these crystals on average contain only less than three mol of zinc$^{++}$ per mole of insulin hexamer (G.D. Smith et al., Proc. Natl. Acad. Sci. USA: 81, pages 7093–7097).

SUMMARY OF THE INVENTION

The object of the present invention is to find insulin derivatives which have an increased zinc binding power, form a stable complex comprising insulin hexamer and zinc$^{++}$ and have a delayed profile of action on subcutaneous injection in comparison with human insulin.

Insulins of the formula I

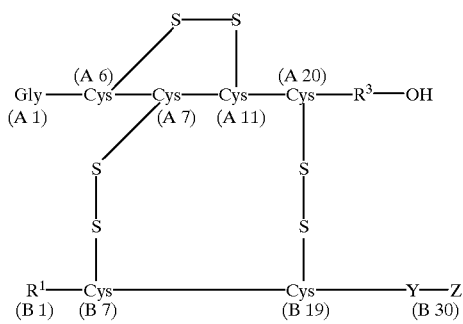

(I)

and/or physiologically tolerable salts of the insulins of the formula I have now been found which fulfill the abovementioned criteria and wherein $R^1$ is a phenylalanine residue or a hydrogen atom,
$R^3$ is a genetically encodable amino acid residue,
Y is a genetically encodable amino acid residue,
Z is
  a) the amino acid residue His or
  b) a peptide having 2 to 35 genetically encodable amino acid residues, of which 1 to 5 are histidine residues,
and the residues A2–A20 correspond to the amino acid sequence of the A chain of human insulin, animal insulin or an insulin derivative and the residues B2–B29 correspond to the amino acid sequence of the B chain of human insulin, animal insulin or an insulin derivative.

An insulin of the formula I is particularly preferred where
  $R^1$ is a phenylalanine residue,
  $R^3$ is an amino acid residue selected from the group consisting of Asn, Gly, Ser, Thr, Ala, Asp, Glu and Gln,
  Y is an amino acid residue selected from the group consisting of Ala, Thr, Ser and His,
  Z is
    a) the amino acid residue His or
    b) a peptide having 4 to 7 amino acid residues, of which 1 or 2 are histidine residues.

An insulin of the formula I is furthermore preferred where
  $R^1$ is a phenylalanine residue,
  $R^3$ is an amino acid residue selected from the group consisting of Asn, Gly, Ser, Thr, Ala, Asp, Glu and Gln,
  Y is an amino acid residue selected from the group consisting of Ala, Thr, Ser and His,
  Z is
    a) the amino acid residue His or
    b) a peptide having 2 to 7 amino acid residues, of which 1 or 2 are histidine residues.

An insulin of the formula I is particularly preferred where
  Z is a peptide having 1 to 5 amino acid residues, of which 1 or 2 are histidine residues.

An insulin of the formula I is particularly preferred, where
  $R^1$ is a phenylalanine residue,
  $R^3$ is an amino acid residue selected from the group consisting of Asn and Gly,
  Y is an amino acid residue selected from the group consisting of Thr and His, and
  Z is a peptide having 1 to 5 amino acid residues, of which 1 or 2 are histidine residues.

An insulin of the formula I is furthermore preferred where $R^1$ is a phenylalanine residue, $R^3$ is a glycine residue, Y is a threonine residue and Z is a peptide having 1 to 5 amino acid residues, of which 1 or 2 are histidine residues.

An insulin of the formula I is very particularly preferred where Z is a peptide having the sequence His His, His His Arg, Ala His His, Ala His His Arg, Ala Ala His His Arg (Seq. ID No.17) or Ala Ala His His (Seq. ID No.18).

The amino acid sequence of peptides and proteins is indicated from the N-terminal end of the amino acid chain onward. The details given in brackets in formula I, e.g. A1, A6, A7, A11, A20, B1, B7, B19 or B30, correspond to the position of amino acid residues in the A or B chains of the insulin.

The expression "genetically encodable amino acid residue" represents the residues of the amino acids Gly, Ala, Ser, Thr, Val, Leu, Ile, Asp, Asn, Glu, Gln, Cys, Met, Arg, Lys, His, Tyr, Phe, Trp, Pro and selenocysteine.

The expressions "residues A2–A20" and "residues B2–B 29" of animal insulin are understood, for example, as meaning the amino acid sequences of insulin from cattle, pigs or chickens.

The expression "residues A2–A20 and B2–B29" of insulin derivatives represents the corresponding amino acid sequences of human insulin which are formed by the replacement of amino acids by other genetically encodable amino acids.

The A chain of human insulin has the following sequence (Seq ID No. 1): Gly, Ile, Val, Glu, Gln, Cys, Cys, Thr, Ser, Ile, Cys, Ser, Leu, Tyr, Gln, Leu, Glu, Asn, Tyr, Cys, Asn.

The B chain of human insulin has the following sequence (Seq ID No. 2): Phe, Val, Asn, Gln, His, Leu, Cys, Gly, Ser, His, Leu, Val, Glu, Ala, Leu, Tyr, Leu, Val, Cys, Gly, Glu, Arg, Gly, Phe, Phe, Tyr, Thr, Pro, Lys, Thr.

The insulin derivative of the formula I can be formed in microorganisms with the aid of a multiplicity of genetic engineering constructs (EP 0 489 780, EP 0 347 781, EP 0 368 187, EP 0 453 969). The genetic engineering constructs are expressed in microorganisms such as *Escherichia coli* or *Streptomycetes* during fermentation. The proteins formed are stored in the interior of the microorganisms (EP 0 489 780) or secreted into the fermentation solution.

Exemplary insulins of the formula I are:
Gly(A21)-human insulin-His(B31)-His(B32)-OH
Gly(A21)-human insulin-His(B31)-His(B32)-Arg (B33)-OH
Gly(A21)-human insulin-Ala(B31)-His(B32)-His(B33)-OH
Gly(A21)-human insulin-Ala(B31)-His(B32)-His(B33)-Arg (B34)-OH
Gly(21)-human insulin-Ala(B31 )-Ala(B32)-His(B33)-His (B34)-OH
Gly(A21)-human insulin-Ala(B31)-Ala(B32)-His(B33)-His (B34)-Arg(B35)-OH The insulin derivatives of the formula I are mainly prepared by genetic engineering by means of site-directed mutagenesis according to standard methods. For this purpose, a gene structure coding for the desired insulin derivative of the formula I is constructed and expressed in a host cell—preferably in a bacterium such as *E. coli* or a yeast, in particular *Sacchamomyces cerevisiae*—and—if the gene structure codes for a fusion protein—the insulin derivative of the formula I is released from the fusion protein; analogous methods are described, for example, in EP-A-0 211 299, EP-A-0 227 938, EP-A-0 229 998, EP-A-0 286 956 and the DE Patent Application P 38 21 159.

After cell disruption, the fusion protein portion may be cleaved chemically by means of cyanogen halide—see EP-A-0 180 920—or enzymatically by means of lysostaphin or trypsin—see DE-A-37 39 347.

The insulin precursor is then subjected to oxidated sulfitolysis according to the method described, for example, by R. C. Marshall and A. S. Inglis in "Practical Protein Chemistry—A Handbook" (Editor A. Darbre) 1986, pages 49–53 and then renatured in the presence of a thiol with formation of the correct disulfide bridges, e.g., according to the method described by G. H. Dixon and A. C. Wardlow in Nature (1960), pages 721–724. The insulin precursors, however, can also be directly folded (EP-A-0 600 372; EP-A-0 668 292).

The C peptide and, if present, the presequence ($R^2$ according to formula II) is removed by means of tryptic cleavage—e.g. according to the method of Kemmler et al., J. B. C. (1971), pages 6786–6791 and the insulin derivative of the formula I is purified by means of known techniques such as chromatography—e.g., EP-A-0 305 760—and crystallization.

The invention further relates to complexes comprising an insulin hexamer and approximately 5 to 9 mol of zinc$^{++}$ per insulin hexamer, preferably 5 to 7 mol of zinc$^{++}$ per insulin hexamer, the insulin hexamer comprising six insulin molecules of the formula I.

The zinc binding to the insulin hexamer is so firm that the 5 to 9 mol of zinc$^{++}$ per mole of insulin hexamer cannot be removed by 40 hours of normal dialysis, for example, with an aqueous 10 mM TRIS/HCl buffer, pH 7.4.

After subcutaneous administration, insulins of the formula I, in an essentially zinc-free preparation (pH 4), show a very small delay in action in comparison with human insulin. After addition of approximately 20 μg of zinc$^{++}$/ml of preparation, a later onset of action is observed after subcutaneous administration. The delay in action is preferably observed at 40 μg of zinc$^{++}$/ml. Higher zinc concentrations enhance this effect.

The invention furthermore relates to preproinsulin of the formula II $$R^2\text{-}R^1\text{-}B2\text{-}B29\text{-}Y\text{-}Z^1\text{-}Gly\text{-}A2\text{-}A20\text{-}R^3 \qquad (II)$$

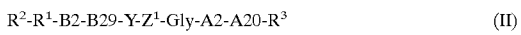

where $R^3$ and Y as in formula I are defined as set forth in one or more of claims 1 to 6, and $R^1$ is a phenylalanine residue or a covalent bond, and $R^2$ is
a) a genetically encodable amino acid residue or
b) a peptide having 2 to 45 amino acid residues, and the residues A2–A20 and B2–B29 correspond to the amino acid sequences of the A and B chains of human insulin, animal insulin or an insulin derivative, and $Z^1$ is a peptide having 2 to 40 genetically encodable amino acid residues, of which 1 to 5 are histidine residues.

The proinsulin of the formula II is suitable as an intermediate in the preparation of the insulins of the formula I.

Preferred proinsulins of the formula II are those where $R^2$ is a peptide having 2 to 25 amino acid residues.

Particularly preferred proinsulins of the formula II are those where $R^2$ is a peptide having 2 to 15 amino acid residues, in which an amino acid residue is selected from the group consisting of Met, Lys and Arg at the carboxyl end.

The insulin derivatives of the formula I and/or the complexes according to the invention, comprising an insulin hexamer and 5 to 9 mol of zinc$^{++}$ per hexamer and/or their physiologically tolerable salts (e.g. the alkali metal or ammonium salts), are mainly used as active compounds for a pharmaceutical preparation for the treatment of diabetes, in particular of diabetes mellitus.

The pharmaceutical preparation is preferably a solution or suspension for injection purposes; it comprises at least one insulin derivative of the formula I and/or the complex according to the invention and/or at least one of its physiologically tolerable salts in dissolved, amorphous and/or crystalline—preferably in dissolved—form.

The preparation preferably has a pH from approximately 2.5 to 8.5, in particular from approximately 4.0 to 8.5, comprising a suitable isotonicizing agent, a suitable preservative and, if appropriate, a suitable buffer, and preferably also a specific zinc ion concentration, all, of course, in sterile aqueous solution. The whole of the preparation apart from the active compound forms the carrier solution.

Preparations comprising solutions of the insulin of the formula I have a pH from 2.5 to 4.5, in particular from 3.5 to 4.5, preferably 4.0.

Preparations comprising suspensions of the insulin of the formula I have a pH from 6.5 to 8.5, in particular from 7.0 to 8.0, preferably 7.4.

Suitable isotonicizing agents are, for example, glycerol, glucose, mannitol, NaCl, calcium compounds or magnesium compounds, such as $CaCl_2$ or $MgCl_2$.

As a result of the choice of the isotonicizing agent and/or preservative, the solubility of the insulin derivative or of its physiologically tolerable salts is affected at the weakly acidic pHs.

Suitable preservatives are, for example, phenol, m-cresol, benzyl alcohol and/or p-hydroxybenzoic acid esters.

Buffer substances which can be used, in particular for adjusting a pH of between approximately 4.0 and 8.5, are, for example sodium acetate, sodium citrate or sodium phosphate. Otherwise, physiologically acceptable dilute acids (typically HCl) or alkalis (typically NaOH) are also suitable for adjusting the pH.

If the preparation comprises zinc$^{++}$, one of from 1 µg to 2 mg of zinc$^{++}$/ml, in particular from 5 µg to 200 µg of zinc$^{++}$/ml, is preferred.

To vary the profile of action of the preparation according to the invention, unmodified insulin, preferably bovine, porcine or human insulin, in particular human insulin, or modified insulins, for example, monomeric insulins, rapid-acting insulins or Gly(A21)-Arg(B31)-Arg(B32)-human insulin, can also be admixed.

Preferred active compound concentrations are those corresponding to approximately 1–1500, more preferably approximately 5–1000, and in particular, approximately 40–400, international units/ml.

EXAMPLE 1

Preparation of Gly(A21)-human Insulin-His(B31)-His(B32)-OH

The preparation of the expression system was carried out essentially as in U.S. Pat. No. 5,358,857, incorporated by reference herein. The vectors pINT 90d and pINT 91d (see Example 17 of the '857 patent) and the PCR primers TIR and Insu11 are also described there. These four components are used, inter alia, as starting materials for the vector constructs described in the following paragraphs.

First, the codon for Gly (A21) was inserted in the sequence coding for the mini-proinsulin. To do this, pINT 91d was used as a template and a PCR reaction was carried out with the primers TIR and Insu31 (Seq ID No. 10):

5' TTT TTT GTC GAC CTA TTA GCC GCA GTA GTT CTC CAG CTG 3'.

The PCR cycle was carried out as follows. 1st minute 94° C., 2nd minute 55° C., 3rd minute 72° C. This cycle was repeated 25 times then the mixture is incubated at 72° C. for 7 minutes and subsequently at 4° C. overnight.

The resulting PCR fragment was precipitated in ethanol to purify it, dried and then digested in restriction buffer using the restriction enzymes NcO1 and Sal1 according to the details of the manufacturers. The reaction mixture was then separated by gel electrophoresis and the NcO1-preproinsulin-Sal1 fragment was isolated. DNA of the plasmid pINT90d is likewise cleaved using NcO1 and Sal1 and the monkey proinsulin fragment was in this manner released from the pINT residual plasmid. Both fragments were separated by gel electrophoresis and the residual plasmid DNA was isolated. This DNA was reacted with the NcO1-Sal1 PCR fragment in a ligase reaction. The plasmid pINT150d was thus obtained, which after transformation by *E. coli,* is replicated and then reisolated.

DNA of the plasmid pINT150d was used as a starting material for the plasmid pINT302, which allowed the preparation of the desired insulin variant.

For the construction of this plasmid, the route described in U.S. Pat. No. 5,358,857 (see Example 6) was taken. Two PCR reactions which are independent of one another were carried out to this end, for which DNA of the plasmid pINT150d was used as a template. One reaction was carried out using the primer pair TIR and pINT B5. (Seq ID No.11):

5' GAT GCC GCG GTG GTG GGT CTT GGG TGT GTAG 3' and the other reaction was carried out using the primer pair Insu11 and pINT B6 (Seq ID No.12):

5' A CCC AAG ACC CAC CAC CGC GGC ATC GTG GAG 3'.

The PCR fragments which resulted were partially complementary, so that in a third PCR reaction they led to a fragment which coded for a Gly (A21) miniproinsulin lengthened by the position B31 and B32. This fragment was cleaved using NcO1 and Sal1 and then reacted with the DNA of the described pINT90d residual plasmid in a ligase reaction to give the plasmid pINT302. An *E. coli* K12 W3110 transformed with this plasmid was then fermented and worked up as in Example 4 of U.S. Pat. No. 5,227,293, incorporated by reference herein. The preproinsulin derivative obtained as intermediate (before trypsin cleavage) had the following amino acid sequence: Preproinsulin 1 (Seq ID No. 3):

Met Ala Thr Thr Ser Thr Gly Asn Ser Ala Arg
Phe Val Asn Gln His Leu Cys Gly Ser His Leu Val Glu Ala Leu
Tyr Leu Val Cys Gly Glu Arg Gly Phe Phe Tyr Thr Pro Lys Thr
His His Arg
Gly Ile Val Glu Gln Cys Cys Thr Ser Ile Cys Ser
Leu Tyr Gln Leu Glu Asn Tyr Cys Gly

Preproinsulin 1 corresponded to the formula II, in this case $R^2$ was a peptide having 11 amino acid residues, $R^1$ was Phe (B1), Y was Thr (B30), $Z^1$ was His His Arg (B31–B33), $R^3$ was Gly (A21) and A2–A20 was the amino acid sequence of the A chain of human insulin (amino acid residues 2 to 20) and B2–B29 was the amino acid sequence of the B chain of human insulin (amino acid residues 2 to 29).

The preproinsulin 1 was cleaved with trypsin as in U.S. Pat. No. 5,227,293 according to Example 4. The product obtained was then reacted with carboxypeptidase B according to Example 11 to give insulin 1. Insulin 1 corresponded to the formula I, in this case $R^1$ was Phe (B1), Y was Thr (B30), Z was His His (B31–B32), $R^3$ was Gly (A21) and A2–A20 was the amino acid sequence of the A chain of human insulin (amino acid residues 2 to 20) and B2–B29 was the amino acid sequence of the B chain of human insulin (amino acid residues 2 to 29).

Insulin 1 had the following amino acid sequence:
Insulin 1 (Seq ID No. 4):
B chain: Phe Val Asn Gln His Leu Cys Gly Ser His Leu Val Glu Ala Leu
Tyr Leu Val Cys Gly Glu Arg Gly Phe Phe Tyr Thr Pro Lys Thr
His His;
A chain: Gly Ile Val Glu Gln Cys Cys Thr Ser Ile Cys Ser Leu Tyr Gln Leu Glu Asn Tyr Cys Gly.

Disulfide bridges were formed as described in formula I.

EXAMPLE 2

Preparation of Gly(A21)-human Insulin-Ala(B31)-His(B32)-His(B33)-Arg(B34)-OH

The expression vector was constructed according to Example 1. Plasmid pINT150d was used as the template for two PCR reactions, which were independent of one another, with the primer pairs TIR and pINT B7 (Seq ID No. 13):

5' GAT GCC GCG GTG GTG CGC GGT CTT GGG TGT GTAG 3', or insu11 and pINT B8 (Seq ID No. 14):

5' ACCC AAG ACC GCG CAC CAC CGC GGC ATC GTG GAG 3'.

The PCR fragments to which both reactions lead were partially complementary and in a third PCR reaction afforded the complete sequence which coded for the desired insulin variant. The fragment of the reaction was treated with the enzymes NcO1 and SaI1 and then ligated into the NcO1/SaI1-opened residual plasmid of the pINT90d DNA. Plasmid pINT303 resulted, which after transformation by *E. coli* K12 W3110, was used as a basis for the expression of the desired pre-miniproinsulin. Fermentation and working up was carried out as in Example 1, the carboxypeptidase B reaction being dispensed with.

The preproinsulin derivative obtained had the following amino acid sequence:

Preproinsulin 2 (Seq ID No. 5):
Met Ala Thr Thr Ser Thr Gly Asn Ser Ala Arg
Phe Val Asn Gln His Leu Cys Gly Ser His Leu Val Glu Ala Leu
Tyr Leu Val Cys Gly Glu Arg Gly Phe Phe Tyr Thr Pro Lys Thr
Ala His His Arg
Gly Ile Val Glu Gln Cys Cys Thr Ser Ile Cys Ser
Leu Tyr Gln Leu Glu Asn Tyr Cys Gly Preproinsulin 2 corresponded to the formula II, in this case $R^1$ was Phe (B1), $R^2$ was a peptide having 11 amino acid residues, Y was Thr (B30), $Z^1$ was Ala His His Arg (B31–B34), $R^3$ was Gly (A21) and A2–A20 was the amino acid sequence of the A chain of human insulin (amino acid residues 2 to 20) and B2–B29 was the amino acid sequence of the B chain of human insulin (amino acid residues 2 to 29).

The preproinsulin 2 was then reacted with trypsin to give insulin 2. Insulin 2 corresponded to the formula II, in this case $R^1$ was Phe (B1), Y was Thr (B30), $Z^1$ was Ala His His Arg (B31–B34), $R^3$ was Gly (A21) and A2–A20 was the amino acid sequence of the A chain of human insulin (amino acid residues 2 to 20) and B2–B29 was the amino acid sequence of the B chain of human insulin (amino acid residues 2 to 29).

Insulin 2 had the following amino acid sequence:
Insulin 2 (Seq ID No. 6):
B chain: Phe Val Asn Gln His Leu Cys Gly Ser His Leu Val Glu Ala Leu
Tyr Leu Val Cys Gly Glu Arg Gly Phe Phe Tyr Thr Pro Lys Thr
Ala His His Arg;
A chain: Gly Ile Val Glu Gln Cys Cys Thr Ser Ile Cys Ser
Leu Tyr Gln Leu Glu Asn Tyr Cys Gly.

Disulfide bridges were formed as described in formula I.

EXAMPLE 3

Preparation of Gly(A21)-human Insulin-Ala(B31)-Ala(B32)-His(B33)-His(B34)-OH

The expression vector was constructed according to Example 1. Plasmid pINT150d is used as the template for two PCR reactions, which were independent of one another, with the primer pairs TIR and pINT 316a (Seq ID No. 15):

5' GAT GCC GCG ATG ATG CGC CGC GGT CTT GGG TGT GTA G 3' or Insu11 and pINT 316b (Seq ID No. 16):

5' A CCC AAG ACC GCG GCG CAT CAT CGC GGC ATC GTG GAG 3'.

The PCR fragments to which both reactions lead were partially complementary and in a third PCR reaction afforded the complete sequence which coded for the desired insulin variant. The fragment of the reaction was treated with the enzymes NcO1 and SaI1 and then ligated into the NcO1/SaI1-opened residual plasmid of the pINT90d DNA. Plasmid pINT316 resulted, which after transformation by *E. coli* K12 W3110, was used as a basis for the expression of the desired pre-miniproinsulin. Fermentation and working up were carried out as in Example 1, the carboxypeptidase B reaction being dispensed with.

The preproinsulin 3 obtained had the following amino acid sequence:

Preproinsulin 3 (Seq ID No.7):
Met Ala Thr Thr Ser Thr Gly Asn Ser Ala Arg
Phe Val Asn Gln His Leu Cys Gly Ser His Leu Val Glu Ala Leu
Tyr Leu Val Cys Gly Glu Arg Gly Phe Phe Tyr Thr Pro Lys Thr
Ala Ala His His Arg
Gly Ile Val Glu Gln Cys Cys Thr Ser Ile Cys Ser
Leu Tyr Gln Leu Glu Asn Tyr Cys Gly Preproinsulin 3 corresponded to the formula II, in this case $R^1$ was Phe (B1), $R^2$ was a peptide having 11 amino acid residues, Y was Thr (B30), $Z^1$ was Ala Ala His His Arg (B31–B35), $R^3$ was Gly (A21) and A2–A20 was the amino acid sequence of the A chain of human insulin (amino acid residues 2 to 20) and B2–B29 was the amino acid sequence of the B chain of human insulin (amino acid residues 2 to 29).

The preproinsulin 3 was then reacted with trypsin and carboxypeptidase B according to Example 11 to give insulin 3. Insulin 3 corresponded to the formula I, in this case $R^1$ was Phe (B1), Y was Thr (B30), Z was Ala Ala His His (B31–B34), $R^3$ was Gly (A1) and A2–A20 was the amino acid sequence of the A chain of human insulin (amino acid residues 2 to 20) and B2–B29 was the amino acid sequence of the B chain of human insulin (amino acid residues 2 to 29).

Insulin 3 had the following amino acid sequence:
Insulin 3 (Seq ID No.8):
B chain: Phe Val Asn Gln His Leu Cys Gly Ser His Leu Val Glu Ala Leu
Tyr Leu Val Cys Gly Glu Arg Gly Phe Phe Tyr Thr Pro Lys Thr
Ala Ala His His;
A chain: Giy Ile Val Giu Gln Cys Cys Thr Ser Ile Cys Ser Leu Tyr Gln Leu Giu Asn Tyr Cys Gly.
Disulfide bridges were formed as described in formula I.

EXAMPLE 4
Insulin 2 Prepared According to Example 2 was Reacted with Carboxypeptidase B According to Example 11 to Give Insulin 4

Insulin 4 corresponded to the formula I, in this case
$R^1$ was Phe (B1),
Y was Thr (B30),
Z was Ala His His (B31–B33),
$R^3$ was Gly (A21) and
A2–A20 was the amino acid sequence of the A chain of human insulin (amino acid residues 2 to 20) and B2–B29 was the amino acid sequence of the B chain of human insulin (amino acid residues 2 to 29).

Insulin 4 had the following amino acid sequence:
Insulin 4 (Seq ID No. 9):
B chain: Phe Val Asn Gln His Leu Cys Gly Ser His Leu Val Glu Ala Leu
Tyr Leu Val Cys Gly Glu Arg Gly Phe Phe Tyr Thr Pro Lys Thr
Ala His His;
A chain: Gly Ile Val Glu Gln Cys Cys Thr Ser Ile Cys Ser Leu Tyr Gln Leu Glu Asn Tyr Cys Gly.
Disulfide bridges were formed as described in formula 1.

EXAMPLE 5
Zinc Binding of Insulin Derivatives

A preparation of insulin (0.243 mM human insulin, 0.13 M NaCl, 0.1 % phenol, 80 µg/ml (1.22 mM) of zinc$^{++}$, 10 mM TRIS/HCl, pH 7.4) was dialyzed at 15° C. against 10 mM TRIS/HCl pH 7.4 for a total of 40 hours (buffer exchange after 16 h and 24 h). The dialyzates were then acidified and the concentration of insulin is determined by HPLC and zinc by atomic absorption spectroscopy. The zinc values were corrected using the zinc content of a control batch which contained no insulin. Table 1 shows the results:

TABLE 1

| Comparison insulins | mol of Zn/mol of insulin hexamer |
|---|---|
| Human insulin (HI) | 1.98 |
| Gly(A21)Des(B30)-HI | 1.8 |
| Gly(A21)Arg(B31)-Arg(B32)-HI | 2.1 |

Insulins of the formula I according to the invention:

| Insulin of the formula I | mol of Zn/mol of insulin hexamer |
|---|---|
| Gly(A21)His(B31)His(B32)-HI | 6.53 |
| Gly(A21)His(B31)His(B32)Arg(B33)-HI | 5.29 |
| Gly(A21)Ala(B31)His(B32)His(B33)-HI | 6.73 |
| Gly(A21)Ala(B31)His(B32)His(B33)Arg(B34)-HI | 5.01 |

EXAMPLE 6
Zinc Dependence of the Profile of Action of Human Insulin in the Dog
Administration: Subcutaneous
Dose: 0.3 IU/kg; pH of the preparation 4.0
Number of dogs (n) per experiment is 6
Table 2 shows the blood glucose in % of the starting value.

TABLE 2*

| Time (h) | Zinc-free | 80 µg of Zn/ml | 160 µg of Zn/ml |
|---|---|---|---|
| 0 | 100 | 100 | 100 |
| 0.5 | 88.66 | 94.06 | 101.48 |
| 1 | 59.73 | 72.31 | 76.87 |
| 1.5 | 50.61 | 58.6 | 67.44 |
| 2 | 54.32 | 54.05 | 61.49 |
| 3 | 61.94 | 58.84 | 62.8 |
| 4 | 85.59 | 70.03 | 71.32 |
| 5 | 100.46 | 78.97 | 81.65 |
| 6 | 105.33 | 94.63 | 96.19 |
| 7 | 106 | 102.46 | 100.27 |
| 8 | 108.39 | 106.12 | 104.34 |
| 10 | 102.72 | 105.11 | 105.1 |
| 12 | 105.03 | 107.14 | 103.02 |

*The numbers printed in bold in Tables 2–6 indicate the lowest blood glucose level achieved by the particular formulation.

EXAMPLE 7
Profile of Action of Gly(A21)Ala(B31)His(B32),His(B33), Arg(B34) Human Insulin in the Dog (Insulin 2)

The insulin 2 prepared according to Example 2 was employed in the following formulation:

Glycerol 20 mg/ml, m-cresol 2.7 mg/ml, insulin 2 40 IU/ml IU resents international units and corresponds to approximately 6 nmol of insulin e.g. human insulin or insulin of the formula I. The pH was adjusted using NaOH or HCl.

Administration: Subcutaneous.
Dose: 0.3 IU/kg;
Number of dogs tested 6.
pH of the preparation 4.0
Table 3 shows the blood glucose in % of the starting value.

TABLE 3

| Time (h) | Zinc-free | 20 µg of Zn/ml | 40 µg of Zn/ml | 80 µg of Zn/ml |
|---|---|---|---|---|
| 0 | 100 | 100 | 100 | 100 |
| 1 | 74.38 | 95.24 | 95.6 | 102.06 |
| 2 | 48.27 | 90.11 | 78.74 | 97.44 |
| 3 | 57.67 | 89.96 | 84.81 | 90.44 |
| 4 | 74.2 | 81.35 | 74.66 | 88.69 |
| 5 | 91.68 | 74.43 | 75.71 | 79.7 |
| 6 | 100.79 | 71.61 | 67.37 | 65.26 |
| 7 | 98.5 | 67.73 | 66.05 | 62.17 |
| 8 | 100.54 | 68.92 | 64.97 | 47.71 |

EXAMPLE 8
Profile of Action of Gly(A21)Ala(B31)His(B32),His(B33) Human Insulin in the Dog (Insulin 4)

The insulin 4 prepared according to Example 4 was formulated and employed as in Example 7.

Administration: Subcutaneous.
Dose: 0.3 IU/kg.
n=6
pH of the preparation 4.0
Table 4 shows the blood glucose in % of the starting value.

TABLE 4

| Time (h) | Zinc-free | 20 μg of Zn/ml | 40 μg of Zn/ml | 80 μg of Zn/ml |
|---|---|---|---|---|
| 0 | 100 | 100 | 100 | 100 |
| 1 | 61.51 | 70 | 96.52 | 101.77 |
| 2 | 49.82 | 52.55 | 89.28 | 90.01 |
| 3 | 55.66 | 60.13 | 80.23 | 70.79 |
| 4 | 78.09 | 78.46 | 73.03 | 68.48 |
| 5 | 94.27 | 97.7 | 70.3 | 74.94 |
| 6 | 103.69 | 105.27 | 61.86 | 74.1 |
| 7 | 105.51 | 106.48 | 62.28 | 76.42 |
| 8 | 108.05 | 104.51 | 81.68 | 88 |

EXAMPLE 9

Profile of Action of Gly(A21)His(B31),His(B32) Human Insulin in the Dog (Insulin 1)

The insulin 1 prepared according to Example 1 was formulated and employed as in Example 7.

Administration: Subcutaneous.
Dose: 0.3 IU/kg.
n=6.
pH of the preparation 4.0

Table 5 shows the blood glucose in % of the starting value.

TABLE 5

| Time (h) | Zinc-free | 20 μg of Zn/ml | 40 μg of Zn/ml | 80 μg of Zn/ml |
|---|---|---|---|---|
| 0 | 100 | 100 | 100 | 100 |
| 1 | 60.71 | 73.16 | 100.25 | 102.86 |
| 2 | 52.29 | 55.43 | 94.86 | 100.19 |
| 3 | 61.74 | 61.6 | 89.37 | 89.12 |
| 4 | 79.93 | 81.53 | 81.55 | 79.19 |
| 5 | 96.17 | 96.84 | 73.06 | 70.67 |
| 6 | 103.2 | 102.43 | 74.58 | 75.75 |
| 7 | 110.86 | 104.75 | 77.68 | 79.36 |
| 8 | 113.42 | 108.14 | 84.87 | 78.74 |

EXAMPLE 10

Profile of Action of Gly(A21)Ala(B31)Ala(B32)His(B33)His(B34) Human Insulin in the Dog (Insulin 3)

The insulin 3 prepared according to Example 1 was formulated and as in Example 7.

Administration: Subcutaneous.
Dose: 0.3 IU/kg.
n=6.
pH of the preparation 4.0.

Table 6 shows the blood glucose in % of the starting value.

TABLE 6

| Time (h) | Zinc-free | 20 μg of Zn/ml | 40 μg of Zn/ml | 80 μg of Zn/ml |
|---|---|---|---|---|
| 0 | 100 | 100 | 100 | 100 |
| 1 | 75 | 99 | 101 | 99 |
| 2 | 57 | 77 | 96 | 91 |
| 3 | 58 | 64 | 84 | 80 |
| 4 | 82 | 65 | 73 | 79 |
| 5 | 94 | 70 | 68 | 77 |
| 6 | 100 | 74 | 72 | 76 |
| 7 | 96 | 81 | 80 | 69 |
| 8 | 100 | 90 | 88 | 75 |
| 9 | 100 | 96 | 94 | 83 |
| 10 | 95 | 98 | 92 | 87 |
| 12 | 98 | 99 | 95 | 94 |
| 14 | 95 | 100 | 94 | 93 |

EXAMPLE 11

Preparation of Insulin from Preproinsulin 1

200 mg of the insulin, one Arg being on the carboxy terminus of the B chain, prepared according to Example 1 was dissolved in 95 ml of 10 mM HCl. After addition of 5 ml of 1 M TRIS/HCl (TRIS(hydroxymethyl)aminomethane) pH 8, the pH was adjusted to 8 using HCl or NaOH.

0.1 mg of carboxypeptidase B was added. After 90 minutes, the cleavage of the arginine was complete. The mixture was adjusted to pH 3.5 by addition of HCl and pumped onto a reversed phase column (PLRP-S RP 300 10μ, 2.5×30 cm, Polymer Laboratories Amherst, Mass., USA). The mobile phase A was water with 0.1% trifluoroacetic acid. Phase B consisted of acetonitrile with 0.09% trifluoroacetic acid. The column was operated at a flow rate of 5 ml/min. After application, the column was washed with 150 ml of A. The fractional elution was carried out by applying a linear gradient of 22.5 to 40% B in 400 minutes. The fractions were analyzed individually by analytical reversed phase HPLC and those which contained Des-Arg-insulin of sufficient purity were combined. The pH was adjusted to 3.5 using NaOH and the acetonitrile was removed in a rotary evaporator. The Des-Arg-insulin was then precipitated by setting a pH of 6.5. The precipitate was centrifuged off, washed twice with 50 ml of water and finally freeze-dried. The yield was 60 to 80% of insulin 1.

What is claimed is:

1. An insulin of the formula I

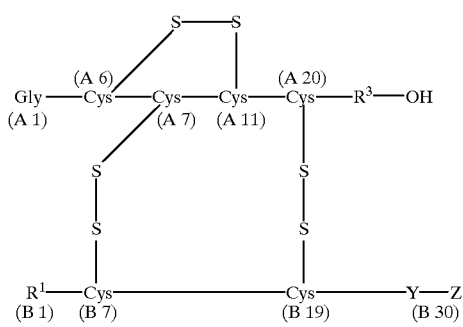
(I)

or a physiologically tolerable salt of the insulin of the formula I, where
- $R^1$ is a phenylalanine residue or a hydrogen atom,
- $R^3$ is glycine,
- Y is a genetically encodable amino acid residue,
- Z is
  - a) the amino acid residue His or
  - b) a peptide having 2 to 35 genetically encodable amino acid residues, having 1 to 5 histidine residues, and the residues A2–A20 correspond to the amino acid sequence of the A chain of insulin or an insulin derivative and the residues B2–B29 correspond to the amino acid sequence of the B chain of insulin or an insulin derivative.

2. An insulin of the formula I as claimed in claim 1, where
- $R^1$ is a phenylalanine residue,
- $R^3$ is glycine,
- Y is an amino acid residue from the group consisting of Ala, Thr, Ser and His,
- Z is
  - a) the amino acid residue His or
  - b) a peptide having 4 to 7 amino acid residues, having 1 or 2 histidine residues.

3. An insulin of the formula I as claimed in claim 1, where
- $R^1$ is a phenylalanine residue,
- $R^3$ is glycine,
- Y is an amino acid residue from the group consisting of Ala, Thr, Ser and His,
- Z is
  - a) the amino acid residue His or
  - b) a peptide having 2 to 7 amino acid residues, having 1 or 2 histidine residues.

4. An insulin of the formula I as claimed in claim 3, where
Z is a peptide having 1 to 5 amino acid residues, of which 1 or 2 are histidine residues.

5. An insulin of the formula I as claimed in claim 1, where
$R^1$ is a phenylalanine residue,
$R^3$ is glycine,
Y is an amino acid residue from the group consisting of Thr and His, and
Z is a peptide having 1 to 5 amino acid residues, having 1 or 2 histidine residues.

6. An insulin of the formula I as claimed in claim 1, where
$R^1$ is a phenylalanine residue,
$R^3$ is a glycine residue,
Y is a threonine residue, and
Z is a peptide having 1 to 5 amino acid residues.

7. An insulin of the formula I as claimed in claim 6, where
Z is a peptide having the sequence His His, His His Arg, Ala His His, Ala His His Arg, Ala Ala His His Arg (Seq. ID No.17) or Ala Ala His His (Seq. ID No.18).

8. A complex comprising an insulin hexamer comprising an insulin of the formula I

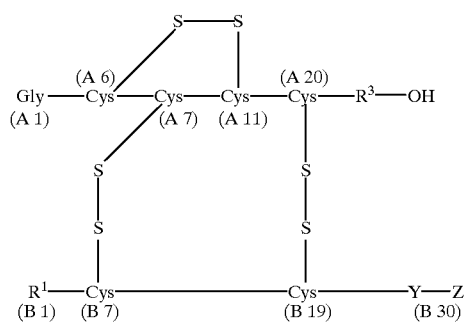

(I)

or a physiologically tolerable salt of the insulin of the formula I, where $R^1$ is a phenylalanine residue or a hydrogen atom,
$R^3$ is a genetically encodable amino acid residue,
Y is a genetically encodable amino acid residue,
Z is
  a) the amino acid residue His or
  b) a peptide having 2 to 35 genetically encodable amino acid residues, having 1 to 5 histidine residues, and the residues A2–A20 correspond to the amino acid sequence of the A chain of insulin or an insulin derivative and the residues B2–B29 correspond to the amino acid sequence of the B chain of insulin or an insulin derivative; and 5 to 9 mol of zinc$^{++}$ per mol of insulin hexamer, the insulin hexamer consisting of six insulin molecules of the formula I.

9. A complex comprising an insulin hexamer comprising an insulin of the formula I

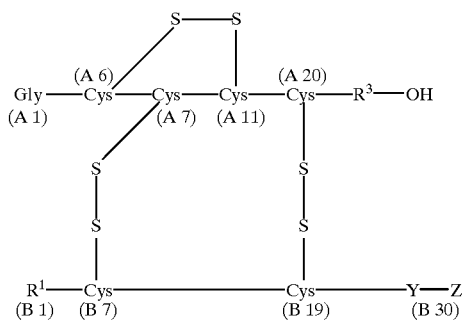

(I)

or a physiologically tolerable salt of the insulin of the formula I, where $R^1$ is a phenylalanine residue or a hydrogen atom,
$R^3$ is a genetically encodable amino acid residue,
Y is a genetically encodable amino acid residue,
Z is
  a) the amino acid residue His or
  b) a peptide having 2 to 35 genetically encodable amino acid residues, having 1 to 5 histidine residues.

and the residues A2–A20 correspond to the amino acid sequence of the A chain of insulin or an insulin derivative and the residues B2–B29 correspond to the amino acid sequence of the B chain of insulin or an insulin derivative; and 5 to 7 mol of zinc$^{++}$ per mol of insulin hexamer, the insulin hexamer comprising six insulin molecules of the formula I.

10. A pharmaceutical preparation, comprising at least one insulin of the formula I and/or at least one physiologically tolerable salt of the insulin of the formula I

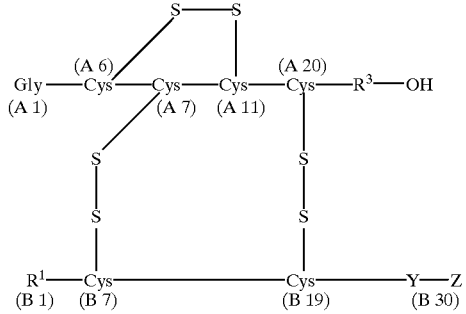

(I)

or a physiologically tolerable salt of the insulin of the formula I, where $R^1$ is a phenylalanine residue or a hydrogen atom,
$R^3$ is glycine,
Y is a genetically encodable amino acid residue,
Z is
  a) the amino acid residue His or
  b) a peptide having 2 to 35 genetically encodable amino acid residues, having 1 to 5 histidine residues, and the residues A2–A20 correspond to the amino acid sequence of the A chain of insulin or an insulin derivative and the residues B2–B29 correspond to the amino acid sequence of the B chain of insulin or an insulin derivative; in dissolved, amorphous and/or crystalline form.

11. A pharmaceutical preparation as claimed in claim 10, further comprising 1 µg to 2 mg of zinc$^{++}$/ml.

12. A pharmaceutical preparation as claimed in claim 10, further comprising 5 μg to 200 μg of zinc$^{++}$/ml.

13. A pharmaceutical preparation as claimed in claim 10, which has a pH of 2.5 to 8.5.

14. A pharmaceutical preparation as claimed in claim 10, which has a pH of 2.5 to 4.5.

15. A pharmaceutical preparation as claimed in claim 10, further comprising unmodified insulin or modified insulin.

16. A pharmaceutical preparation as claimed in claim 10, further comprising Gly(A21)-Arg(B31)-Arg(B32)-human insulin.

17. A proinsulin of the formula II $$R^2\text{-}R^1\text{-}B2\text{-}B29\text{-}Y\text{-}Z^1\text{-}Gly\text{-}A2\text{-}A20\text{-}R^3 \qquad (II)$$

where $R^3$ and Y as in formula I are defined as set forth in claim 1, and $R^1$ is a phenylalanine residue or a covalent bond, and
$R^2$ is
  a) a genetically encodable amino acid residue or
  b) a peptide having 2 to 45 amino acid residues, and the residues A2–A20 and B2–B29 correspond to the amino acid sequences of the A and B chains of human insulin, animal insulin or an insulin derivative, and $Z^1$ is a peptide having 2 to 40 genetically encodable amino acid residues, of which 1 to 5 are histidine residues.

18. A proinsulin of the formula II as claimed in claim 17, where
$R^2$ is a peptide having 2 to 25 amino acid residues.

19. A proinsulin of the formula II as claimed in claim 17, where
$R^2$ is a peptide having 2 to 15 amino acid residues, in which a carboxyl end amino acid residue is selected from the group consisting of Met, Lys and Arg.

20. The insulin of the formula I as claimed in claim 1, wherein the residues A2–A20 correspond to the amino acid sequence of the A chain of human insulin.

21. The insulin of the formula I as claimed in claim 1, wherein the residues B2–B29 correspond to the amino acid sequence of the B chain of human insulin.

22. The pharmaceutical preparation as claimed in claim 15, wherein the unmodified insulin is human insulin.

* * * * *